US012594241B2

(12) United States Patent
Sudhakar et al.

(10) Patent No.: US 12,594,241 B2
(45) Date of Patent: Apr. 7, 2026

(54) TOPIRAMATE ORAL LIQUID SUSPENSION AND USE THEREOF

(71) Applicant: OWP Pharmaceuticals, Inc., Naperville, IL (US)

(72) Inventors: Paul Sudhakar, Shawnee, KS (US); Scott Boyer, West Chicago, IL (US)

( * ) Notice: Subject to any disclaimer, the term of this patent is extended or adjusted under 35 U.S.C. 154(b) by 0 days.

(21) Appl. No.: 18/462,651

(22) Filed: Sep. 7, 2023

(65) Prior Publication Data

US 2023/0414503 A1      Dec. 28, 2023

Related U.S. Application Data

(63) Continuation of application No. 17/643,818, filed on Dec. 10, 2021, now Pat. No. 11,759,421, which is a continuation of application No. 16/946,132, filed on Jun. 8, 2020, now Pat. No. 11,197,825.

(60) Provisional application No. 62/858,415, filed on Jun. 7, 2019.

(51) Int. Cl.
| | |
|---|---|
| *A61K 9/08* | (2006.01) |
| *A61K 9/00* | (2006.01) |
| *A61K 31/36* | (2006.01) |
| *A61K 47/10* | (2017.01) |
| *A61K 47/12* | (2006.01) |
| *A61K 47/26* | (2006.01) |
| *A61K 47/38* | (2006.01) |

(52) U.S. Cl.
CPC .............. *A61K 9/08* (2013.01); *A61K 9/0053* (2013.01); *A61K 31/36* (2013.01); *A61K 47/10* (2013.01); *A61K 47/12* (2013.01); *A61K 47/26* (2013.01); *A61K 47/38* (2013.01)

(58) Field of Classification Search
CPC .... A61K 47/02; A61K 47/26; A61K 31/7048; A61K 47/12; A61K 9/0095; A61K 31/36; A61K 47/38; A61K 9/0056; A61K 47/14; A61K 47/10; A61K 9/10; A61K 47/36; A61P 1/00; Y02A 50/30
See application file for complete search history.

(56) References Cited

PUBLICATIONS

"Handbook of Pharmaceutical Excipients," Rowe et al., Eds., 8th Edition, Pharmaceutical Press (2017).
Danilo Arnone, Review of the use of Topiramate for treatment of psychiatric disorders, 4(5) Annals of General Psychiatry (2005).
Final Office Action, U.S. Appl. No. 17/643,820, filed Apr. 10, 2023, 8 pgs.
Kaufman, Antiepileptic Drugs in The Treatment of Psychiatric Disorders, Epilepsy & Behavior, 21, pp. 1-11. (Year: 2011).
Medline Plus Drug Information, Topiramate, pp. 1-8, retrieved Feb. 8, 2021 (Year: 2021).
NAMI: National Alliance on Mental Illness, Mental Health Conditions, pp. 1-6, Retrieved Feb. 8, 2021 (Year: 2021).
Non-Final Office Action, U.S. Appl. No. 16/946,132, filed Feb. 17, 2021, 11 pgs.
Non-Final Office Action, U.S. Appl. No. 16/951,869, filed Feb. 12, 2021, 12 pgs.
Non-Final Office Action, U.S. Appl. No. 17/643,820, filed Jul. 18, 2023, 6 pgs.
Non-Final Office Action, U.S. Appl. No. 17/643,820, filed Nov. 9, 2022, 11 pgs.
Notice of Allowability, U.S. Appl. No. 16/946,132, filed Jul. 23, 2021, 5 pgs.
Notice of Allowability, U.S. Appl. No. 16/951,869, filed Jul. 9, 2021, 5 pgs.
Notice of Allowance and Fee(s) Due, U.S. Appl. No. 16/946,132, filed Jul. 8, 2021, 8 pgs.
Notice of Allowance and Fee(s) Due, U.S. Appl. No. 16/951,869, filed May 20, 2021, 9 pgs.
Notice of Allowance and Fee(s) Due, U.S. Appl. No. 17/643,818, filed Aug. 4, 2023, 5 pgs.
Response to Final Office Action, U.S. Appl. No. 17/643,820, filed Jun. 28, 2023, 11 pgs.
Response to Non-Final Office Action, U.S. Appl. No. 17/643,820, filed Dec. 29, 2022, 8 pgs.
Response to Non-Final Office Action, U.S. Appl. No. 17/643,820, filed Jul. 21, 2023, 7 pgs.

*Primary Examiner* — Lezah Roberts
(74) *Attorney, Agent, or Firm* — Carlson, Caspers, Vandenburgh & Lindquist, P.A.

(57) ABSTRACT

Provided herein is an oral liquid suspension that includes topiramate, as well as methods of medical treatment that include orally administering the oral liquid suspension.

29 Claims, No Drawings

TOPIRAMATE ORAL LIQUID SUSPENSION AND USE THEREOF

RELATED U.S. APPLICATION DATA

This application is a continuation of U.S. application Ser. No. 17/643,818, filed Dec. 10, 2021, now U.S. Pat. No. 11,759,421, issued Sep. 19, 2023, which is a continuation of U.S. application Ser. No. 16/946,132, filed Jun. 8, 2020, now U.S. Pat. No. 11,197,825, issued Dec. 14, 2021, which claims the benefit of priority to provisional patent application No. 62/858,415 filed on Jun. 7, 2019; the contents of which are incorporated by reference herein in their entirety.

BACKGROUND OF THE INVENTION

Epilepsy is a disease of the nervous system which is caused by brain dysfunction due to excessive discharge of the nerve cells in the brain. It is estimated that the incidence rate of epilepsy is from about 0.3% to 0.5% globally. The morbidity rate is from about 5 to 10 people per 1000 people. Epilepsy is a serious threat to people's health and affects their daily lives.

Topiramate is an antiepileptic drug and its chemical structure relates to amino-sulfamate monosaccharide. Topiramate was first developed by Johnson & Johnson Company, Inc. USA. It was marketed under the brand name of Topamax in the UK in 1995. Based on in-vitro studies of neurons in electrophysiological and biochemical experiments, it was found that there were three mechanisms of antiepileptic action. Firstly, topiramate blocks the neuron's depolarization, which indicates that it can block sodium channels. Secondly, topiramate can increase the frequency of activation of γ-aminobutyrate (GABA) receptors by GABA and enhance the ability of influx of chloride ions which indicates that topiramate can enhance the role of inhibitory central neurotransmitters. Thirdly, topiramate can reduce the activity of glutamate AMPA receptors which indicates that topiramate can reduce the effect of excitatory central neurotransmitters.

Topiramate is a white crystalline powder with a bitter taste. It is freely soluble in acetone, dimethyl sulfoxide, ethanol, and alkaline solutions containing sodium hydroxide or sodium phosphate. Its solubility in water is approximately 9.8 mg/mL at room temperature.

Thus, to obtain a topiramate formulation with stable chemical properties and/or desired sustained release effect is highly desirable.

SUMMARY OF THE INVENTION

The present invention provides for an oral liquid suspension that includes: topiramate, preservative, sweetener, solvent, anticaking agent, viscosifying agent, suspending agent, pH adjuster, and taste-masking agent.

The present invention also provides for an oral liquid suspension that includes: topiramate, preservative, sweetener, solvent, anticaking agent, viscosifying agent, suspending agent, flavoring agent, colorant, pH adjuster, and taste-masking agent.

The present invention also provides for an oral liquid suspension that includes: 2,3:4,5-Di-O-isopropylidene-β-D-fructopyranose sulfamate (topiramate); water; glycerin; propylene glycol polyethylene glycol; methylparaben; sodium benzoate; sorbitol saccharin; sucralose; xanthan gum, carboxymethyl cellulose (CMC); sodium phosphate; and PROSOLV® SMCC 50M (microcrystalline cellulose and colloidal silicon dioxide).

The present invention also provides for an oral liquid suspension that includes:

| Amount (% w/v) | Component |
|---|---|
| 2.5 ± 0.25 | topiramate |
| 0.10 ± 0.01 | methylparaben |
| 0.03 ± 0.003 | sodium benzoate powder |
| 0.08 ± 0.008 | saccharin sodium dihydrate |
| 3.00 ± 0.3 | 70% solution of sorbitol |
| 2.25 ± 0.3 | propylene glycol |
| 5 ± 0.5 | glycerin (99% natural) |
| 1.26 ± 0.15 | PROSOLV ® SMCC 50M (microcrystalline cellulose and colloidal silicon dioxide) |
| 0.18 ± 0.02 | sodium carboxymethyl cellulose (medium viscosity, 2% aqueous solution at 25° C. 400-800 cPs) |
| 0.18 ± 0.02 | xanthan gum NF |
| 0.20 ± 0.02 | cherry flavor, natural & artificial |
| 0.002 ± 0.0002 | FD&C Red #40 |
| 0.0002 ± 0.00002 | FD&C Yellow #6 |
| 79.67 ± 8.0 | purified water |
| 5 ± 0.5 | polyethylene glycol 400 |
| 0.25 ± 0.03 | sodium phosphate dibasic (dried) |
| 0.5 ± 0.05 | sucralose |

The composition described herein is an oral liquid suspension and not, e.g., an oral solution. As such, the active ingredient, topiramate, is not fully dissolved but is essentially suspended therein. While the active ingredient may be only slightly dissolved therein, the lack of it being fully dissolved could otherwise pose stability issues. As an oral liquid suspension, the active ingredient will typically settle to the bottom of the container during extended periods of time during the shipmen and storage. Effectively resuspending the active ingredient will need to be carried out prior to use. Additionally, the active ingredient (topiramate) is unpleasant tasting.

The composition described herein is an oral liquid suspension that includes a suspending agent, viscosifying agent, anticaking agent, and redispersing agent. Achieving a suitable stability of the suspended active ingredient is achieved in part by modifying the pH of the composition. Achieving a suitable stability of the suspended active ingredient is also achieved in part by controlling the particle size distribution as well as the water content of the active ingredient. Including a suitable flavoring agent provides a composition that is relatively pleasant tasting. The oral liquid suspension, compared to the solid oral dosage form (e.g., tablets) containing topiramate, is therefore (i) convenient to use, (ii) has a relatively quick onset of action, (iii) can be used with children and the elderly who often have difficulties swallowing, and (iv) the dose can readily be titrated. Additionally, the above is achieved while providing for an oral liquid suspension (v) having a suitable redispersibility, (vi) is relatively stable, (vii) is relatively pleasant tasting, (viii) upon shaking will be substantially devoid of lumps or clumps, even after long storage, (ix) possesses good pourability, (x) has good physical stability properties such as low level of sedimentation (reduced or no caking), (xi) has easy redispersion on agitation, and (xii) provides for dose uniformity during each administration.

The present invention also provides for a method for treating at least one of a neurological disorder and a mental disorder in a subject. The method includes administering to a subject suffering from the disorder an oral liquid suspension described herein.

US 12,594,241 B2

3

DETAILED DESCRIPTION OF THE
INVENTION

The present invention can be more readily understood by
reading the following detailed description of the invention
and study of the included examples.

The present invention is based, in part, upon the discovery
of novel oral liquid suspensions that provide advantages
when used for the in vivo delivery to a mammal of the active
pharmaceutical ingredient (API) topiramate. In doing so, the
present invention provides for oral liquid suspensions that
provide for a suitable therapeutic index and/or lower inci-
dence, severity, or duration of adverse reaction(s) compared
to previously described dosage forms containing the active
ingredient in the same amount.

The oral liquid suspensions may be used for a variety of
purposes, including for the in vivo delivery of the active
pharmaceutical ingredient (API) topiramate. Accordingly,
the present invention further provides methods of treating
diseases or disorders (e.g., neurological disorder and/or a
mental disorder), such as epilepsy and/or bipolar disorder.

Relative to oral tablets or chewable dispersible tablets
containing an equivalent amount of topiramate, administra-
tion of the oral liquid suspension may result in a lower
incidence, severity, and/or duration of adverse reactions
including at least one of dizziness, headache, diplopia,
ataxia, nausea, blurred vision, somnolence, rhinitis, pharyn-
gitis, rash, vomiting, infection, fever, accidental injury,
diarrhea, abdominal pain, tremor, insomnia, somnolence,
backpain, fatigue, abdominal pain, and xerostomia.

In forming an oral liquid suspension, any one or more of
the excipients employed can effectively be dissolved or
dispersed therein (e.g., in the solvent). This includes, e.g.,
salts, such as sodium benzoate, saccharin sodium, and
sodium carboxymethyl cellulose. In doing so, the salt can
dissociate into the respective anion and cation, and would
therefore no longer necessarily exist in the salt form—
benzoic acid, saccharin, and carboxymethyl cellulose. How-
ever, within the context of the invention, it is appreciated
that those of skill in the art understand and agree that
reference to the oral liquid suspension as containing the salt
form is otherwise acceptable and appropriate.

Likewise, in specific embodiments, topiramate (having a
specified particle size distribution (PSD)) can be employed
in the manufacture of the oral liquid suspension. In forming
the oral liquid suspension, the topiramate present therein can
effectively be suspended and/or dissolved therein (e.g., in
the solvent). In doing so, the topiramate would therefore no
longer necessarily retain the PSD. However, within the
context of the invention, it is appreciated that those of skill
in the art understand and agree that reference to the oral
liquid suspension as containing the topiramate as having a
specified PSD (based on the topiramate employed) is oth-
erwise acceptable and appropriate. Alternatively, reference
to the oral liquid suspension as containing the topiramate as
having a specified PSD (based on the topiramate present in
the oral liquid suspension) is also acceptable and appropri-
ate. As such, the PSD of the topiramate employed is often a
parameter for the PSD of topiramate present in the oral
liquid suspension.

The articles "a" and "an" as used herein refers to "one or
more" or "at least one," unless otherwise indicated. That is,
reference to any element or component of an embodiment by
the indefinite article "a" or "an" does not exclude the
possibility that more than one element or component is
present.

4

The term "excipient" refers to a pharmacologically inac-
tive component present in the oral liquid suspension. Excipi-
ents include, e.g., preservatives, sweetening agents, sol-
vents, anticaking agents, viscosity-increasing agents,
suspending agents, acidifying agents, flavoring agents, and
colorants. The excipients used in preparing the oral liquid
suspension described herein are safe and non-toxic. Suitable
excipients are disclosed in Handbook of Pharmaceutical
Excipients, Rowe et al., Eds., 8th Edition, Pharmaceutical
Press (2017).

The term "preservative" refers to a substance that is added
to products, such as oral liquid suspensions, to prevent
decomposition by microbial growth or by undesirable
chemical changes. In general, preservation is implemented
in two modes, chemical and physical. Suitable preservatives
include, e.g., one or more of ethanol, benzoic acid, benzyl
alcohol, bronopol, butylated hydroxyanisole (BHA),
butylparaben, calcium acetate, calcium chloride, calcium
lactate, cetrimide, cetylpyridinium chloride, chlorhexidine,
chlorobutanol, chlorocresol, chloroxylenol, citric acid
monohydrate, ethylparaben, glycerin, hexetidine, imidurea,
isopropyl alcohol, lactic acid, methylparaben, monothio-
glycerol, parabens, pentetic acid, phenoxyethanol, phenyl-
ethyl alcohol, potassium benzoate, potassium metabisulfite,
potassium sorbate, propionic acid, propyl gallate, propylene
glycol, propylparaben, propylparaben sodium, sodium
acetate, sodium benzoate, sodium borate, sodium lactate,
sodium metabisulfite, sodium propionate, sodium sulfite,
sorbic acid, sulfobutyl ether ß-cyclodextrin, edetic acid,
thimerosal, and xanthan.

The term "sweetening agent" or "sweetener" refers to a
substance that is added to products, such as oral liquid
suspensions, to provide a sweet taste like that of sugar. The
sweetener can include, e.g., one or more of acesulfame
potassium, alitame, aspartame, dextrose, erythritol, fructose,
glycerin, isomalt, lactitol, glucose, maltitol, maltose, man-
nitol, monk fruit extract, neohesperidin dihydrochalcone,
neotame, saccharin, saccharin sodium, sodium cyclamate,
sorbitol, *stevia*, sucralose, sucrose, tagatose, thaumatin,
trehalose, and xylitol.

The term "solvent" refers to a substance that is added to
products, such as oral liquid suspensions, to dissolve the
active pharmaceutical ingredient (API) and/or excipients.
The solvent can include, e.g., one or more of albumin,
ethanol, almond oil, benzyl alcohol, benzyl benzoate, buty-
lene glycol, castor oil, corn oil (maize), cottonseed oil,
dimethyl ether, dimethylacetamide, ethyl lactate, ethyl
oleate, glycerin, isopropyl alcohol, isopropyl myristate, iso-
propyl palmitate, light mineral oil, medium-chain triglycer-
ides, methyl lactate, mineral oil, monoethanolamine, octyl-
dodecanol, olive oil, peanut oil, polyethylene glycol,
polyoxyl castor oil, propylene carbonate, propylene glycol,
pyrrolidone, safflower oil, sesame oil, soybean oil, sunflower
oil, triacetin, tricaprylin, triethanolamine, triethyl citrate,
triolein, and water.

The term "anticaking agent" refers to a substance that is
added to products, such as oral liquid suspensions, to
prevent or decrease the occurrence of agglomeration of
particles, such as the active pharmaceutical ingredient (API)
and/or excipients. The anticaking agent is added to prevent
or decrease the formation of lumps (caking), which provides
for ease in packaging, transport, flowability, and consump-
tion. The anticaking agent can include, e.g., one or more of
tribasic calcium phosphate, calcium silicate, colloidal sili-
con dioxide, hydrophobic colloidal silica, magnesium oxide,
magnesium silicate, magnesium trisilicate, and talc.

The term "viscosity-increasing agent" refers to a substance that is added to products, such as oral liquid suspensions, to increase the viscosity. The viscosity increasing agent is used in order to impart an appropriate viscosity to the oral liquid suspension. The viscosity increasing agent increases the viscosity of the oral liquid suspension without substantially changing its other properties. The viscosity-increasing agent can include, e.g., one or more of acacia, agar, alginic acid, bentonite, carboxymethylcellulose calcium, carboxymethylcellulose sodium, carrageenan, *ceratonia*, cetostearyl alcohol, chitosan, colloidal silicon dioxide, cyclomethicone, ethylcellulose, gelatin, glycerin, guar gum, hectorite, hydrogenated vegetable oil type I, hydrophobic colloidal silica, hydroxyethyl cellulose, hydroxyethylmethyl cellulose, hydroxypropyl cellulose, hydroxypropyl starch, hypromellose, magnesium aluminum silicate, maltodextrin, methylcellulose, myristyl alcohol, polydextrose, polyethylene glycol, polyvinyl alcohol, potassium chloride, povidone, propylene glycol alginate, saponite, sodium alginate, sodium chloride, starch, stearyl alcohol, sucrose, sulfobutyl ether ß-cyclodextrin, tragacanth, and xanthan gum.

The term "suspending agent" refers to a substance that helps the active pharmaceutical ingredient (API) stay suspended in the oral liquid suspension and prevents caking at the bottom of the container. One of the properties of a well-formulated oral liquid suspension is that it can be easily re-suspended by the use of moderate agitation or shaking. The suspending agent can include, e.g., one or more of acacia, agar, alginic acid, bentonite, calcium stearate, carbomers, carboxymethylcellulose calcium, carboxymethylcellulose sodium, carrageenan, powdered cellulose, cellulose, microcrystalline cellulose, carboxymethylcellulose sodium, *ceratonia*, colloidal silicon dioxide, dextrin, gelatin, guar gum, hectorite, hydrophobic colloidal silica, hydroxyethyl cellulose, hydroxyethylmethyl cellulose, hydroxypropyl cellulose, hypromellose, kaolin, magnesium aluminum silicate, maltitol solution, medium-chain triglycerides, methylcellulose, silicified microcrystalline cellulose, phospholipids, polycarbophil, polyethylene glycol, polyoxyethylene sorbitan fatty acid esters, potassium alginate, povidone, propylene glycol alginate, saponite, sesame oil, sodium alginate, sodium starch glycolate, sorbitan esters, sucrose, tragacanth, vitamin E polyethylene glycol succinate, and xanthan gum. Additionally, the suspending agent can include, e.g., PROSOLV® SMCC 50M (microcrystalline cellulose and colloidal silicon dioxide).

The suspending agent is able to reduce the formation of topiramate hydrate. In some embodiments, less than about 8 wt. %, less than about 5 wt. %, less than about 3 wt. %, less than about 1 wt. %, or less than about 0.5 wt. % of the topiramate thereof is converted into its hydrate form over the period of time of manufacturing, shipping, and storage of the oral liquid suspension described herein (e.g., up to 6-9 months) under ambient conditions.

The suspending agent also contributes to the stability of the suspension after reconstitution. In some embodiments, less than about 5 wt. %, less than about 3 wt. %, less than about 1 wt. %, less than about 0.5 wt. %, less than about 0.2 wt. %, or less than about 0.1 wt. % of the topiramate is decomposed over the period of time of manufacturing, shipping, and storage of the oral liquid suspension described herein (e.g., up to 6-9 months) under ambient conditions.

The term "acidifying agent" refers to a substance that is added to products, such as oral liquid suspensions, to lower the pH, or is added to achieve a desired pH that is lower than it would otherwise be in the absence of the acidifying agent. The acidifying agent can include, e.g., one or more of sodium phosphate dibasic, adipic acid, ammonium chloride, citric acid monohydrate, diluted hydrochloric acid, lactic acid, propionic acid, and tartaric acid.

The term "flavoring agent" refers to a substance that gives another substance flavor, altering the characteristics of the solute, causing it to become sweet, sour, tangy, etc. A flavor is a quality of something that affects the sense of taste. The flavoring agent can include, e.g., cherry flavor, grape, or peppermint.

The term "colorant" or "coloring agent" refers to substance that is added or applied in order to change the color of a material or surface. Colorants work by absorbing varying amounts of light at different wavelengths (or frequencies) of its spectrum, transmitting (if translucent) or reflecting the remaining light in straight lines or scattered. The colorant can include, e.g., FD&C red #40, FD&C yellow #6, or a combination thereof.

The term "oral liquid suspension" refers to a pharmaceutical dosage form that is a liquid and is orally administered. It includes topiramate mixed with a liquid vehicle for oral administration. Being a suspension, the dosage form consists of undissolved particles (e.g., topiramate and/or excipients). The undissolved particles can be suspended in the oral liquid suspension. Alternatively, the undissolved particles can settle to the bottom of the container where it can be shaken and/or agitated to resuspend in the solution.

The term "topiramate" refers to the compound chemically designated as 2,3.4,5-Di-O-isopropylidene-β-D-fructopyranose sulfamate. Topiramate has the molecular formula $C_{12}H_{21}NO_8S$ and a molecular weight of 339.36. In specific embodiments, the topiramate functions as the sole active ingredient. The topiramate used herein will also have a suitable particle size distribution (PSD). Topiramate, unless otherwise specified, includes the free base, pharmaceutically acceptable salts thereof, isomers, and polymorphs thereof. Topiramate is commercially available in multiple physical forms (e.g., amorphous or crystalline forms). A micronized amorphous form is commercially available from Polpharma (Poland).

The term "glycerin" or "glycerol" refers to the compound chemically designated as propane-1,2,3-triol, having the chemical formula $C_3H_8O_3$ and molar mass 92.094 g/mol. The glycerin can be glycerin, 99% natural. When present in the oral liquid suspension described herein, the glycerin can function as a preservative, sweetening agent, solvent, viscosity-increasing agent, or any combination thereof.

The term "propylene glycol" refers to the compound chemically designated as propane-1,2-diol, having the chemical formula $C_3H_8O_2$, and molar mass 76.095 g/mol. When present in the oral liquid suspension described herein, the propylene glycol can function as a preservative, solvent, viscosity-increasing agent, or any combination thereof.

The term "polyethylene glycol" or "PEG" refers to the compound chemically designated as poly(oxyethylene) or PEO (also referred to as poly(ethylene oxide) or PEO), having the chemical formula $C_{2n}H_{4n+2}O_{n+1}$, and molar mass 18.02+44.05n g/mol. PEG, PEO, and POE refer to an oligomer or polymer of ethylene oxide. The three names are chemically synonymous, but historically PEG is preferred in the biomedical field, whereas PEO is more prevalent in the field of polymer chemistry. Because different applications require different polymer chain lengths, PEG has tended to refer to oligomers and polymers with a molecular mass below 20,000 g/mol, PEO to polymers with a molecular mass above 20,000 g/mol, and POE to a polymer of any molecular mass. PEGs are typically prepared by polymerization of ethylene oxide and are commercially available over a wide range of molecular weights from 300 g/mol to 10,000,000 g/mol. When present in the oral liquid suspension described herein, the polyethylene glycol can function as a solvent, viscosity-increasing agent, suspending agent, or any combination thereof.

The polyethylene glycol can be polyethylene glycol 400. The term "polyethylene glycol 400" refers to a low-molecular-weight grade of polyethylene glycol, having the chemical formula $C_{2n}H_{4+2}O_{n+1}$, wherein n=8.2 to 9.1, and molar mass 380-420 g/mol. When present in the oral liquid suspension described herein, the polyethylene glycol 400 can function as a solvent, viscosity-increasing agent, suspending agent, or any combination thereof.

The term "methylparaben" refers to the compound chemically designated as methyl 4-hydroxybenzoate, having the chemical formula $C_8H_8O_3$, and molar mas 152.149 g/mol. When present in the oral liquid suspension described herein, the methylparaben can function as a preservative.

The term "sodium benzoate" refers to the compound benzoate of soda, having the chemical formula $C_7H_5NaO_2$, and molar mass 144.105 g/mol. When present in the oral liquid suspension described herein, the sodium benzoate can function as a preservative.

The term "sorbitol" refers to the compound chemically designated as (2S,3R,4R,5R)-hexane-1,2,3,4,5,6-hexol, having the chemical formula $C_6H_{14}O_6$, and molar mass 182.17 g/mol.

The sorbitol can be solid sorbitol. Alternatively, the sorbitol can be in solution (e.g., 70% solution of sorbitol). When present in the oral liquid suspension described herein, the sorbitol can function as a sweetening agent.

The term "saccharin" refers to the compound chemically designated as 1,1-dioxo-1,2-benzothiazol-3-one, having the chemical formula $C_7H_5NO_3S$, and molar mass 183.18 g/mol. When present in the oral liquid suspension described herein, the saccharin can function as a sweetening agent.

The saccharin can be saccharin sodium dihydrate powder. The term "saccharin sodium" refers to the sodium salt of saccharin. When present in the oral liquid suspension described herein, the saccharin sodium dihydrate powder can function as a sweetening agent.

The term "sucralose" refers to the compound chemically designated as 1,6-dichloro-1,6-dideoxy-β-D-fructofuranosyl-4-chloro-4-deoxy-α-D-galactopyranoside, having the chemical formula $C_{12}H_{19}C_3O_8$, and molar mass 397.64 g/mol. When present in the oral liquid suspension described herein, the sucralose can function as a sweetening agent.

The term "citric acid" refers to the compound chemically designated as 2-hydroxypropane-1,2,3-tricarboxylic acid, having the chemical formula $C_6H_8O_7$, and molar mass 192.123 g/mol (anhydrous) or 210.038 g/mol (monohydrate). When present in the oral liquid suspension described herein, the citric acid can function as an acidifying agent, preservative, or combination thereof.

The term "xanthan gum" refers to a polysaccharide having the CAS Number 11138-66-2, and chemical formula $C_{35}H_{49}O_{29}$ (monomer). When present in the oral liquid suspension described herein, the xanthan gum can function as a viscosity-increasing agent, suspending agent, or a combination thereof.

The term "carboxymethyl cellulose," "carmellose," or "CMC" refers to a cellulose derivative with carboxymethyl groups ($-CH_2-COOH$) bound to some of the hydroxyl groups of the glucopyranose monomers that make up the cellulose backbone. It is often used as its sodium salt, sodium carboxymethyl cellulose. CMC has the CAS Number 9000-11-7. The carboxymethyl cellulose can be sodium carboxymethyl cellulose (medium viscosity, 2% aqueous solution at 25° C. 400-800 cPs). When present in the oral liquid suspension described herein, the carboxymethyl cellulose can function as a viscosity-increasing agent, suspending agent, or combination thereof.

The term "microcrystalline cellulose" or "MCC" is a term for refined wood pulp. A naturally occurring polymer, it is composed of glucose units connected by a 1-4 beta glycosidic bond. These linear cellulose chains are bundled together as microfibril spiraled together in the walls of plant cell. When present in the oral liquid suspension described herein, the microcrystalline cellulose can function as a suspending agent.

The term "silicified microcrystalline cellulose" refers to MCC which is silicified. Silicification is the process in which organic matter becomes saturated with silica. When present in the oral liquid suspension described herein, the silicified microcrystalline cellulose can function as a suspending agent.

The term "disodium phosphate" or "DSP" or "sodium hydrogen phosphate" or "sodium phosphate dibasic" refers to the inorganic compound with the formula $Na_2HPO_4$. and CAS Number 7558-79-4. The disodium phosphate can be sodium phosphate dibasic (dried). When present in the oral liquid suspension described herein, the disodium phosphate can function as a pH modifying agent.

The term "PROSOLV® SMCC" refers to silicified microcrystalline cellulose, which is a combination of microcrystalline cellulose (MCC) and colloidal silicon dioxide (CSD). The commercial product PROSOLV® SMCC 50M has an average particle size determined by laser diffraction (μm) of 65. The commercial product PROSOLV® SMCC 50M also has a bulk density (g/mL) of 0.25-0.37. PROSOLV® SMCC is commercially available from JRS Pharma (Patterson, NY), https://www.jrspharma.com/pharma_en/.

The term "neurological disorder" refers to any disorder of the nervous system. Structural, biochemical or electrical abnormalities in the brain, spinal cord or other nerves can result in a range of symptoms. Such disorders may be diagnosed by a health care professional.

The term "mental disorder" or "psychiatric disorder" refers to a behavioral or mental pattern that causes significant distress or impairment of personal functioning. Such features may be persistent, relapsing and remitting, or occur as a single episode. Many disorders have been described, with signs and symptoms that vary widely between specific disorders. Such disorders may be diagnosed by a mental health professional.

The term "epilepsy" refers to a group of neurological disorders characterized by epileptic seizures. Epileptic seizures are episodes that can vary from brief and nearly undetectable periods to long periods of vigorous shaking. These episodes can result in physical injuries, including occasionally broken bones. In epilepsy, seizures tend to recur and, as a rule, have no immediate underlying cause. Isolated seizures that are provoked by a specific cause such as poisoning are not deemed to represent epilepsy. People with epilepsy may be treated differently in various areas of the world and experience varying degrees of social stigma due to their condition.

The term "focal seizures" or "partial seizures" or "partial onset seizures" refer to localized seizures and are seizures which affect initially only one hemisphere of the brain. The brain is divided into two hemispheres, each consisting of four lobes—the frontal, temporal, parietal and occipital lobes. A focal seizure is generated in and affects just one part of the brain—a whole hemisphere or part of a lobe. Symptoms will vary according to where the seizure occurs.

In the frontal lobe symptoms may include a wave-like sensation in the head; in the temporal lobe, a feeling of déjà vu; in the parietal lobe, numbness or tingling; and in the occipital lobe, visual disturbance or hallucination.

The term "generalized seizures," as opposed to focal seizures, refer to a type of seizure that impairs consciousness and distorts the electrical activity of the whole or a larger portion of the brain (which can be seen, for example, on electroencephalography, EEG.

The term "generalized tonic-clonic seizure" or "grand mal seizure" refers to a type of generalized seizure that produces bilateral, convulsive tonic and clonic muscle contractions. Tonic-clonic seizures are the seizure type most commonly associated with epilepsy and seizures in general and the most common seizure associated with metabolic imbalances. A tonic-clonic seizure is a convulsion that combines the characteristics of tonic (meaning stiffening) and clonic (meaning rhythmical jerking) seizures. The disturbance in functioning is present in both sides of the brain. The tonic phase comes first (e.g., all the muscles stiffen, air being forced past the vocal cords causes a cry or groan, and the person loses consciousness and falls to the floor). After the tonic phase comes the clonic phase (e.g., the arms and usually the legs begin to jerk rapidly and rhythmically, bending and relaxing at the elbows, hips, and knees, and after a few minutes, the jerking slows and stops.).

The term "Lennox-Gastaut syndrome" refers to a complex, rare, and severe childhood-onset epilepsy. It is characterized by multiple and concurrent seizure types, cognitive dysfunction, and slow spike waves on electroencephalogram (EEG). Typically, it presents in children aged 3-5 years and can persist into adulthood. It has been associated with several gene mutations, perinatal insults, congenital infections, brain tumors/malformations, and genetic disorders such as tuberous sclerosis and West syndrome.

The term "generalized seizures of Lennox-Gastaut syndrome" refers to generalized seizures associated with Lennox-Gastaut syndrome.

The term "antiepileptic drug," "anticonvulsant," or "AED" refers to a diverse group of pharmacological agents used in the treatment of epileptic seizures. Anticonvulsants are also increasingly being used in the treatment of bipolar disorder and borderline personality disorder, since many seem to act as mood stabilizers, and for the treatment of neuropathic pain. Anticonvulsants suppress the excessive rapid firing of neurons during seizures. Anticonvulsants also prevent the spread of the seizure within the brain.

The term "bipolar disorder," previously known as manic depression, refers to a mental disorder that causes periods of depression and periods of abnormally elevated mood. The elevated mood is significant and is known as mania or hypomania, depending on its severity, or whether symptoms of psychosis are present. During mania, an individual behaves or feels abnormally energetic, happy, or irritable. Individuals often make poorly thought out decisions with little regard to the consequences. The need for sleep is usually reduced during manic phases. During periods of depression, there may be crying, a negative outlook on life, and poor eye contact with others.

The term "combination therapy," "adjunctive therapy," or "polytherapy" refers to therapy that uses more than one medication or modality (versus "monotherapy," which is any therapy taken alone). Typically, these terms refer to using multiple therapies to treat a single disease, and often all the therapies are pharmaceutical (although it can also involve non-medical therapy, such as the combination of medications and talk therapy to treat depression). Monotherapy can be applied to any therapeutic approach, but it is most commonly used to describe the use of a single medication. Typically, monotherapy is selected because a single medication is adequate to treat the medical condition. However, monotherapies may also be used because of unwanted side effects or dangerous drug interactions.

The particle size of topiramate can be measured by suitable techniques such as laser light scattering (e.g. Malvern Light Scattering), Coulter counter, microscopy, Fraunhofer diffraction and any other technique known in the art. This particle size can be obtained either by the final step during the manufacture of the topiramate or by the use of conventional micronizing techniques after the crystallization procedure(s).

The term "$T_{max}$" refers to time of maximum plasma concentration and is the time to reach maximum (peak) plasma concentration following drug administration. It is measured in units of time (hours).

The term "$t_{1/2}$" refers to elimination half-life and is time to reach elimination half-life (to be used in one or non-compartmental model). It is measured in units of time (hours).

The term "stable" refers to chemical stability, wherein not more than 5 wt. % of total related substances are formed on storage at 40° C. and 75% relative humidity (R.H.) for a period of 90 days.

The term "shaken" refers to shaken prior to use. For example, a medical practitioner or subject (e.g., patient) can shake the oral liquid suspension prior to administration. The shaking can include vigorously shaking by hand, for example, for about 5 to 40 seconds.

The term "release," "released," "releasing," and the like, when used in connection with a pharmaceutical dosage form, refers to the process or the portion of the active ingredient that leaves the dosage form following contact with an aqueous environment. Unless otherwise indicated, the quantity of an active ingredient released from a dosage form is measured by dissolution testing in water as described in this invention. The results of the dissolution testing are reported as a percentage (w/w) released as a function of time or as the release time. In some embodiments, complete release of an active ingredient occurs when at least 90% of the active ingredient has been released from the dosage form.

The term "immediate-release" refers to those which disintegrate rapidly and/or get dissolved to release the medicaments or active ingredient.

The term "sedimentation volume ratio" or "sedimentation ratio" refers to a ratio of the ultimate volume of sediment (Vu) to the original volume of sediment (VO) before settling. The sedimentation volume ratio is generally achieved within about 5 minutes, 3 minutes, 2 minutes, 60 seconds, 45 seconds, or 30 seconds after the powder formulation is reconstituted to the suspension. Various mechanical means, such as shaking, swirling, heating, or any combination thereof can be used to promote a uniform suspension.

The term "subject" refers to a mammal, such as an animal or a human. Hence, the methods disclosed herein can be useful in human therapy and veterinary applications. In one embodiment, the subject is an animal. In another embodiment, the subject is a human.

The term "treat" or "treating" refers to attain or attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition.

The term "$D_{90}$" refers to the particle size corresponding to 90% of the cumulative undersize distribution by volume.

The term "$D_{50}$" refers to the particle size corresponding to 50% of the cumulative undersize distribution by volume.

The term "$D_{10}$" refers to the particle size corresponding to 10% of the cumulative undersize distribution by volume.

It is appreciated that those of skill in the art understand that each of the excipients present in the oral liquid suspension provide for one or more functions. For example, glycerin can function as a preservative, sweetening agent, solvent, viscosity-increasing agent, or any combination thereof. Formulating an oral liquid suspension to contain excipients that provide multiple functions is beneficial and advantageous, for example, as the oral liquid suspension can have a pleasant taste and/or can have a higher drug load (thereby requiring a lower volume to be administered), while achieving the desirable physicochemical properties and technical attributes.

The viscosity can be measured by using as suitable instrument such as Brookfield viscometer, Haake VT 550 viscometer at room temperature (25° C.).

The oral liquid suspension described herein can be packaged in a suitable pack/container such as amber colored polyethylene terephthalate (PET) bottle, glass bottle, high density polyethylene (HDPE) bottle, low density polyethylene (LDPE) bottle, polypropylene (PP) bottle, the like. The glass or plastic bottle can be provided with a child proof closure. The package can include a syringe or cup (marked in mL, ounces, or both) for ease of dosing. The container such as bottle has a fill volume of, e.g., from about 50 mL to about 500 mL containing the topiramate oral liquid suspension. Containers for use in the storage of the oral suspensions may be used to administer a multiple dose of topiramate.

Specific Ranges, Values, Features, and Embodiments

The specific embodiments provided below describing the ranges, values, and features are for illustration purposes only, and do not otherwise limit the scope of the disclosed subject matter, as defined by the claims.

In specific embodiments, the oral liquid suspension includes topiramate, present in 2.5±0.30% (w/v).

In specific embodiments, the oral liquid suspension includes topiramate, present in 2.5±0.25% (w/v).

In specific embodiments, the oral liquid suspension includes topiramate, present in 2.5±0.20% (w/v).

In specific embodiments, the oral liquid suspension includes topiramate, present in 2.5±0.15% (w/v).

In specific embodiments, the oral liquid suspension includes topiramate, present in 2.5±0.10% (w/v).

In specific embodiments, the oral liquid suspension includes topiramate, present in 2.5±0.05% (w/v).

In specific embodiments, the oral liquid suspension includes topiramate, present in 25 mg per milliliter.

In specific embodiments, the oral liquid suspension includes topiramate, present in 25±2.5 mg per milliliter.

In specific embodiments, the oral liquid suspension includes topiramate, present in 25±2.0 mg per milliliter.

In specific embodiments, the oral liquid suspension includes topiramate, present in 25±1.5 mg per milliliter.

In specific embodiments, the oral liquid suspension includes topiramate, present in 25±1.0 mg per milliliter.

In specific embodiments, the oral liquid suspension includes topiramate, present in 25±0.5 mg per milliliter.

In specific embodiments, the oral liquid suspension includes water, present in 79.67±10% (w/v).

In specific embodiments, the oral liquid suspension includes water, present in 79.67±8% (w/v).

In specific embodiments, the oral liquid suspension includes water, present in 79.67±7% (w/v).

In specific embodiments, the oral liquid suspension includes water, present in 79.67±5% (w/v).

In specific embodiments, the oral liquid suspension includes water, present in 79.67±3% (w/v).

In specific embodiments, the oral liquid suspension includes water, present in 79.67±1.5% (w/v).

In specific embodiments, the oral liquid suspension includes glycerin, present in 5±2.0% (w/v).

In specific embodiments, the oral liquid suspension includes glycerin, present in 5±1.0% (w/v).

In specific embodiments, the oral liquid suspension includes glycerin, present in 5±0.75% (w/v).

In specific embodiments, the oral liquid suspension includes glycerin, present in 5±0.50% (w/v).

In specific embodiments, the oral liquid suspension includes glycerin, present in 5±0.25% (w/v).

In specific embodiments, the oral liquid suspension includes propylene glycol, present in 2.25±1.0% (w/v).

In specific embodiments, the oral liquid suspension includes propylene glycol, present in 2.25±0.75% (w/v).

In specific embodiments, the oral liquid suspension includes propylene glycol, present in 2.25±0.5% (w/v).

In specific embodiments, the oral liquid suspension includes propylene glycol, present in 2.25±0.3% (w/v).

In specific embodiments, the oral liquid suspension includes propylene glycol, present in 2.25±0.25% (w/v).

In specific embodiments, the oral liquid suspension includes polyethylene glycol 400, present in 5.00±2.0% (w/v).

In specific embodiments, the oral liquid suspension includes polyethylene glycol 400, present in 5.00±1.0% (w/v).

In specific embodiments, the oral liquid suspension includes polyethylene glycol 400, present in 5.00±0.75% (w/v).

In specific embodiments, the oral liquid suspension includes polyethylene glycol 400, present in 5.00±0.5% (w/v).

In specific embodiments, the oral liquid suspension includes polyethylene glycol 400, present in 5.00±0.25% (w/v).

In specific embodiments, the oral liquid suspension includes methylparaben, present in 0.1±0.05% (w/v).

In specific embodiments, the oral liquid suspension includes methylparaben, present in 0.1±0.04% (w/v).

In specific embodiments, the oral liquid suspension includes methylparaben, present in 0.1±0.03% (w/v).

In specific embodiments, the oral liquid suspension includes methylparaben, present in 0.1±0.02% (w/v).

In specific embodiments, the oral liquid suspension includes methylparaben, present in 0.1±0.01% (w/v).

In specific embodiments, the oral liquid suspension includes sodium benzoate powder, present in 0.03±0.006% (w/v).

In specific embodiments, the oral liquid suspension includes sodium benzoate powder, present in 0.03±0.003% (w/v).

In specific embodiments, the oral liquid suspension includes sodium benzoate powder, present in 0.03±0.002% (w/v).

In specific embodiments, the oral liquid suspension includes sodium benzoate powder, present in 0.03±0.001% (w/v).

In specific embodiments, the oral liquid suspension includes sorbitol, present in 2.1±0.42% (w/v).

In specific embodiments, the oral liquid suspension includes sorbitol, present in 2.1±0.6% (w/v).

In specific embodiments, the oral liquid suspension includes sorbitol, present in 2.1±0.5% (w/v).

In specific embodiments, the oral liquid suspension includes sorbitol, present in 2.1±0.3% (w/v).

In specific embodiments, the oral liquid suspension includes sorbitol, present in 2.1±0.2% (w/v).

In specific embodiments, the oral liquid suspension includes sorbitol, present in 2.1±0.1% (w/v).

In specific embodiments, the oral liquid suspension includes a 70% solution of sorbitol, present in 3.0±0.6% (w/v).

In specific embodiments, the oral liquid suspension includes a 70% solution of sorbitol, present in 3.0±0.4% (w/v).

In specific embodiments, the oral liquid suspension includes a 70% solution of sorbitol, present in 3.0±0.2% (w/v).

In specific embodiments, the oral liquid suspension includes a 70% solution of sorbitol, present in 3.0±0.1% (w/v).

In specific embodiments, the oral liquid suspension includes saccharin sodium dihydrate powder, present in 0.08±0.04% (w/v).

In specific embodiments, the oral liquid suspension includes saccharin sodium dihydrate powder, present in 0.08±0.02% (w/v).

In specific embodiments, the oral liquid suspension includes saccharin sodium dihydrate powder, present in 0.08±0.015% (w/v).

In specific embodiments, the oral liquid suspension includes saccharin sodium dihydrate powder, present in 0.08±0.010% (w/v).

In specific embodiments, the oral liquid suspension includes saccharin sodium dihydrate powder, present in 0.08±0.008% (w/v).

In specific embodiments, the oral liquid suspension includes saccharin sodium dihydrate powder, present in 0.08±0.003% (w/v).

In specific embodiments, the oral liquid suspension includes saccharin sodium dihydrate powder, present in 0.08±0.012% (w/v).

In specific embodiments, the oral liquid suspension includes sucralose, present in 0.5±0.15% (w/v).

In specific embodiments, the oral liquid suspension includes sucralose, present in 0.5±0.10% (w/v).

In specific embodiments, the oral liquid suspension includes sucralose, present in 0.5±0.05% (w/v).

In specific embodiments, the oral liquid suspension includes sucralose, present in 0.5±0.25% (w/v).

In specific embodiments, the oral liquid suspension includes sodium phosphate dibasic (dried), present in 0.25±0.08% (w/v).

In specific embodiments, the oral liquid suspension includes sodium phosphate dibasic (dried), present in 0.25±0.05% (w/v).

In specific embodiments, the oral liquid suspension includes sodium phosphate dibasic (dried), present in 0.25±0.03% (w/v).

In specific embodiments, the oral liquid suspension includes sodium phosphate dibasic (dried), present in 0.25±0.025% (w/v).

In specific embodiments, the oral liquid suspension includes sodium phosphate dibasic (dried), present in 0.25±0.02% (w/v).

In specific embodiments, the oral liquid suspension includes xanthan gum, present in 0.18±0.10%.

In specific embodiments, the oral liquid suspension includes xanthan gum, present in 0.18±0.08%.

In specific embodiments, the oral liquid suspension includes xanthan gum, present in 0.18±0.05%.

In specific embodiments, the oral liquid suspension includes xanthan gum, present in 0.18±0.03%.

In specific embodiments, the oral liquid suspension includes xanthan gum, present in 0.18±0.02%.

In specific embodiments, the oral liquid suspension includes sodium carboxymethyl cellulose (medium viscosity, 2% aqueous solution at 25° C. 400-800 cPs), present in 0.18±0.10% (w/v).

In specific embodiments, the oral liquid suspension includes sodium carboxymethyl cellulose (medium viscosity, 2% aqueous solution at 25° C. 400-800 cPs), present in 0.18±0.08% (w/v).

In specific embodiments, the oral liquid suspension includes sodium carboxymethyl cellulose (medium viscosity, 2% aqueous solution at 25° C. 400-800 cPs), present in 0.18±0.05% (w/v).

In specific embodiments, the oral liquid suspension includes sodium carboxymethyl cellulose (medium viscosity, 2% aqueous solution at 25° C. 400-800 cPs), present in 0.18±0.04% (w/v).

In specific embodiments, the oral liquid suspension includes sodium carboxymethyl cellulose (medium viscosity, 2% aqueous solution at 25° C. 400-800 cPs), present in 0.18±0.02% (w/v).

In specific embodiments, the oral liquid suspension includes PROSOLV® SMCC 50M (microcrystalline cellulose and colloidal silicon dioxide), present in 1.26±0.5% (w/v).

In specific embodiments, the oral liquid suspension includes PROSOLV® SMCC 50M (microcrystalline cellulose and colloidal silicon dioxide), present in 1.26±0.4% (w/v).

In specific embodiments, the oral liquid suspension includes PROSOLV® SMCC 50M (microcrystalline cellulose and colloidal silicon dioxide), present in 1.26±0.3% (w/v).

In specific embodiments, the oral liquid suspension includes PROSOLV® SMCC 50M (microcrystalline cellulose and colloidal silicon dioxide), present in 1.26±0.2% (w/v).

In specific embodiments, the oral liquid suspension includes PROSOLV® SMCC 50M (microcrystalline cellulose and colloidal silicon dioxide), present in 1.26±0.1% (w/v).

In specific embodiments, the oral liquid suspension includes one or more flavoring agents.

In specific embodiments, the oral liquid suspension includes the flavoring agent cherry flavor, natural & artificial.

In specific embodiments, the oral liquid suspension does not include a flavoring agent.

In specific embodiments, the oral liquid suspension includes one or more colorants.

In specific embodiments, the oral liquid suspension includes the colorants FD&C Red #40 and FD&C Yellow #6.

In specific embodiments, the oral liquid suspension does not include a colorant.

In specific embodiments, the oral liquid suspension includes:

| Amount (% w/v) | Component |
|---|---|
| 2.5 ± 0.25 | topiramate |
| 0.10 ± 0.01 | methylparaben |
| 0.03 ± 0.003 | sodium benzoate powder |
| 0.08 ± 0.008 | saccharin sodium dihydrate |
| 3.00 ± 0.3 | 70% solution of sorbitol |
| 2.25 ± 0.3 | propylene glycol |
| 5 ± 0.5 | glycerin (99% natural) |
| 1.26 ± 0.15 | PROSOLV ® SMCC 50M (microcrystalline cellulose and colloidal silicon dioxide) |
| 0.18 ± 0.02 | sodium carboxymethyl cellulose (medium viscosity, 2% aqueous solution at 25° C. 400-800 cPs) |
| 0.18 ± 0.02 | xanthan gum NF |
| 0.20 ± 0.02 | cherry flavor, natural & artificial |
| 0.002 ± 0.0002 | FD&C Red #40 |
| 0.0002 ± 0.00002 | FD&C Yellow #6 |
| 79.67 ± 8.0 | purified water |
| 5 ± 0.5 | polyethylene glycol 400 |
| 0.25 ± 0.03 | sodium phosphate dibasic (dried) |
| 0.5 ± 0.05 | sucralose |

In specific embodiments, the oral liquid suspension has a volume of up to 50 mL.

In specific embodiments, the oral liquid suspension has a volume of up to 20 mL.

In specific embodiments, the oral liquid suspension has a volume of 0.2 mL to 20 mL.

In specific embodiments, the oral liquid suspension has a volume of 0.2 mL, 0.5 mL, 2.5 mL, 10 mL, 15 mL, or 20 mL.

In specific embodiments, the oral liquid suspension has a volume of 0.2 mL.

In specific embodiments, the oral liquid suspension has a volume of 0.5 mL.

In specific embodiments, the oral liquid suspension has a volume of 2.5 mL.

In specific embodiments, the oral liquid suspension has a volume of 10 mL.

In specific embodiments, the oral liquid suspension has a volume of 15 mL.

In specific embodiments, the oral liquid suspension has a volume of 20 mL.

In specific embodiments, the oral liquid suspension has a pH of 7.5-7.9.

In specific embodiments, the oral liquid suspension has a pH of 7.7±0.1.

In specific embodiments, the oral liquid suspension has a viscosity (at 25° C.) of 300-400 mPs.

In specific embodiments, the oral liquid suspension has a viscosity (at 25° C.) of 310-390 mPs.

In specific embodiments, the oral liquid suspension has a viscosity (at 25° C.) of 320-380 mPs.

In specific embodiments, the oral liquid suspension has a viscosity (at 25° C.) of 325-375 mPs.

In specific embodiments, the oral liquid suspension has a viscosity (at 25° C.) of 341.7±20 mPs.

In specific embodiments, the oral liquid suspension has a viscosity (at 25° C.) of 341.7±10 mPs.

In specific embodiments, the oral liquid suspension has a viscosity (at 25° C.) of 341.7±5 mPs.

In specific embodiments, the oral liquid suspension has a specific gravity of not greater than 1.3.

In specific embodiments, the oral liquid suspension has a specific gravity of not greater than 1.25.

In specific embodiments, the oral liquid suspension has a specific gravity of not greater than 1.2.

In specific embodiments, the oral liquid suspension has a specific gravity of not greater than 1.05.

In specific embodiments, the oral liquid suspension has a specific gravity of not greater than 1.049.

In specific embodiments, the oral liquid suspension is packaged in a container.

In specific embodiments, the oral liquid suspension is packaged in an amber colored polyethylene terephthalate (PET) bottle.

In specific embodiments, the oral liquid suspension is packaged in a glass bottle.

In specific embodiments, the oral liquid suspension is packaged in a high density polyethylene (HDPE) bottle.

In specific embodiments, the oral liquid suspension is packaged in a low density polyethylene (LDPE) bottle.

In specific embodiments, the oral liquid suspension is packaged in a polypropylene (PP) bottle.

In specific embodiments, the oral liquid suspension is packaged in a glass or plastic bottle with a child proof closure.

In specific embodiments, the oral liquid suspension is packaged in a glass or plastic bottle and the packaging further includes a syringe or cup, marked in mL, ounces, or both.

In specific embodiments, the oral liquid suspension is packaged in a glass or plastic bottle configured for use to administer multiple doses of topiramate.

In specific embodiments, the oral liquid suspension, while packaged in a container, is free from microbial contamination for a specified period of time (e.g., ≥20 days, ≥30 days, ≥60 days, ≥90 days, ≥180 days, ≥12 months, or ≥24 months) when tested according to <1111>USP-30 NF-25.

In specific embodiments, the oral liquid suspension, while packaged in a container, is free from microbial contamination for an extended period of time encountered with the shipping and storage of the oral liquid suspension.

In specific embodiments, the oral liquid suspension, while packaged in a container, is free from microbial contamination for an extended period of time encountered with the shipping and storage of the oral liquid suspension under ambient conditions, wherein the microbial contamination includes *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.1 wt. % *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.01 wt. % *Escherichia coli* (*E. coli*).

In specific embodiments, the oral liquid suspension, while packaged in a container, is free from microbial contamination for an extended period of time encountered with the shipping and storage of the oral liquid suspension under ambient conditions, wherein the microbial contamination includes *Burkholderia cepacia* complex (BCC).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.1 wt. % *Burkholderia cepacia* complex (BCC).

In specific embodiments, the oral liquid suspension, while packaged in a container, is free from microbial contamination for an extended period of time encountered with the shipping and storage of the oral liquid suspension under ambient conditions, wherein the microbial contamination includes less than 0.01 wt. % *Burkholderia cepacia* complex (BCC).

In specific embodiments, the oral liquid suspension, while packaged in a container, is free from microbial contamination for at least 24 months under ambient conditions.

In specific embodiments, the oral liquid suspension, while packaged in a container, is free from microbial contamination for at least 12 months under ambient conditions.

In specific embodiments, the oral liquid suspension, while packaged in a container, is free from microbial contamination for at least 6 months under ambient conditions.

In specific embodiments, the oral liquid suspension, while packaged in a container, is free from microbial contamination for at least 180 days under ambient conditions.

In specific embodiments, the oral liquid suspension, while packaged in a container, is free from microbial contamination for at least 90 days under ambient conditions.

In specific embodiments, the oral liquid suspension is an immediate release dosage form.

In specific embodiments, the oral liquid suspension exhibits redispersibility.

In specific embodiments, the oral liquid suspension exhibits redispersibility, such that upon turning over 3 times, the oral liquid suspension exhibits at least 80% redispersibility.

In specific embodiments, the oral liquid suspension exhibits redispersibility, such that upon turning over 3 times, the oral liquid suspension exhibits at least 85% redispersibility.

In specific embodiments, the oral liquid suspension exhibits redispersibility, such that upon turning over 3 times, the oral liquid suspension exhibits at least 90% redispersibility.

In specific embodiments, the oral liquid suspension exhibits redispersibility, such that upon turning over 3 times, the oral liquid suspension exhibits at least 95% redispersibility.

In specific embodiments, the oral liquid suspension is an immediate release dosage form that exhibits in-vitro dissolution rate more than 85% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

In specific embodiments, the oral liquid suspension is an immediate release dosage form that exhibits in-vitro dissolution rate more than 88% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

In specific embodiments, the topiramate in the oral liquid suspension has a particle size distribution $D_{90}$ of not more than 200 microns.

In specific embodiments, the topiramate in the oral liquid suspension has a particle size distribution $D_{90}$ of not more than 175 microns.

In specific embodiments, the topiramate in the oral liquid suspension has a particle size distribution $D_{90}$ of not more than 150 microns.

In specific embodiments, the topiramate in the oral liquid suspension has a particle size distribution $D_{90}$ of not more than 140 microns.

In specific embodiments, the topiramate in the oral liquid suspension has a particle size distribution $D_{50}$ of not more than 100 microns.

In specific embodiments, the topiramate in the oral liquid suspension has a particle size distribution $D_{50}$ of not more than 90 microns.

In specific embodiments, the topiramate in the oral liquid suspension has a particle size distribution $D_{50}$ of not more than 80 microns.

In specific embodiments, the topiramate in the oral liquid suspension has a particle size distribution $D_{50}$ of not more than 63 microns.

In specific embodiments, the topiramate in the oral liquid suspension has a particle size distribution $D_{10}$ of not more than 30 microns.

In specific embodiments, the topiramate in the oral liquid suspension has a particle size distribution $D_{10}$ of not more than 29 microns.

In specific embodiments, the topiramate in the oral liquid suspension has a particle size distribution $D_{10}$ of not more than 27 microns.

In specific embodiments, the topiramate in the oral liquid suspension has a particle size distribution $D_{10}$ of not more than 26 microns.

In specific embodiments, the topiramate in the oral liquid suspension has the following particle size distribution:

$D_{90}$ of not more than 200 microns;
$D_{50}$ of not more than 100 microns; and
$D_{10}$ of not more than 30 microns.

In specific embodiments, the topiramate in the oral liquid suspension has the following particle size distribution:

$D_{90}$ of not more than 139 microns;
$D_{50}$ of not more than 64.8 microns; and
$D_{10}$ of not more than 24.65 microns.

In specific embodiments, the topiramate employed in the manufacture of the oral liquid suspension has a particle size distribution $D_{90}$ of not more than 90 microns.

In specific embodiments, the topiramate employed in the manufacture of the oral liquid suspension has a particle size distribution $D_{90}$ of not more than 80 microns.

In specific embodiments, the topiramate employed in the manufacture of the oral liquid suspension has a particle size distribution $D_{90}$ of not more than 70 microns.

In specific embodiments, the topiramate employed in the manufacture of the oral liquid suspension has a particle size distribution $D_{50}$ of not more than 50 microns.

In specific embodiments, the topiramate employed in the manufacture of the oral liquid suspension has a particle size distribution $D_{50}$ of not more than 40 microns.

In specific embodiments, the topiramate employed in the manufacture of the oral liquid suspension has a particle size distribution $D_{50}$ of not more than 30 microns.

In specific embodiments, the topiramate employed in the manufacture of the oral liquid suspension has a particle size distribution $D_{10}$ of not more than 30 microns.

In specific embodiments, the topiramate employed in the manufacture of the oral liquid suspension has a particle size distribution $D_{10}$ of not more than 20 microns.

In specific embodiments, the topiramate employed in the manufacture of the oral liquid suspension has a particle size distribution $D_{10}$ of not more than 10 microns.

In specific embodiments, the topiramate employed in the manufacture of the oral liquid suspension has the following particle size distribution:

$D_{90}$ of not more than 70 microns;

$D_{50}$ of not more than 30 microns; and $D_{10}$ of not more than 10 microns.

In specific embodiments, the topiramate employed in the manufacture of the oral liquid suspension is amorphous.

In specific embodiments, the topiramate employed in the manufacture of the oral liquid suspension is crystalline.

In specific embodiments, the topiramate employed in the manufacture of the oral liquid suspension has a water content of not more than 1.0 wt. %.

In specific embodiments, the topiramate employed in the manufacture of the oral liquid suspension has a water content of not more than 0.75 wt. %.

In specific embodiments, the topiramate employed in the manufacture of the oral liquid suspension has a water content of not more than 0.5 wt. %.

In specific embodiments, the oral liquid suspension is administered to a subject that is a human.

In specific embodiments, the oral liquid suspension is administered to a subject that is a human adult of at least 16 years in age (i.e., aged 16 years or older).

In specific embodiments, the oral liquid suspension is administered to a subject that is a human adult of at least 18 years in age (i.e., aged 18 years or older).

In specific embodiments, the oral liquid suspension is administered to a subject that is a human of less than 16 years in age.

In specific embodiments, the oral liquid suspension is administered to a subject that is a human aged 2 years or older (i.e., aged 2 years or older).

In specific embodiments, the oral liquid suspension is administered to treat at least one of a neurological disorder and a mental disorder in a subject.

In specific embodiments, the oral liquid suspension is administered to treat a neurological disorder in a subject.

In specific embodiments, the oral liquid suspension is administered to treat a mental disorder in a subject.

In specific embodiments, the oral liquid suspension is administered to treat at least one of a neurological disorder and a mental disorder in a subject, wherein the disorder comprises at least one of (a)-(c):

(a) epilepsy-adjunctive therapy in a subject aged 2 years or older:

partial-onset seizures primary generalized tonic-clonic seizures generalized seizures of Lennox-Gastaut syndrome (b) epilepsy-monotherapy in a subject aged 16 years and older: Conversion to monotherapy in a subject with partial-onset seizures who are receiving treatment with carbamazepine, phenytoin, phenobarbital, primidone, or valproate as the single AED (c) bipolar disorder: maintenance treatment of bipolar I disorder to delay the time to occurrence of mood episodes in a subject treated for acute mood episodes with standard therapy.

In specific embodiments, the disorder is epilepsy.

In specific embodiments, the oral liquid suspension is administered as an adjunctive therapy to a subject aged 2 years or older, to treat epilepsy.

In specific embodiments, the oral liquid suspension is administered as an adjunctive therapy to a subject aged 2 years or older, to treat partial-onset seizures.

In specific embodiments, the oral liquid suspension is administered as an adjunctive therapy to a subject aged 2 years or older, to treat primary generalized tonic-clonic seizures.

In specific embodiments, the oral liquid suspension is administered as an adjunctive therapy to a subject aged 2 years or older, to treat generalized seizures of Lennox-Gastaut syndrome.

In specific embodiments, the oral liquid suspension is administered as a monotherapy to a subject aged 16 years or older, to treat epilepsy.

In specific embodiments, the oral liquid suspension is administered as a monotherapy to a subject aged 16 years or older with partial-onset seizures, to treat epilepsy, wherein the subject is undergoing conversion to monotherapy and is receiving treatment with carbamazepine, phenytoin, phenobarbital, primidone, or valproate as the single AED.

In specific embodiments, the oral liquid suspension is administered to a subject to treat bipolar disorder.

In specific embodiments, the oral liquid suspension is administered to a subject for maintenance treatment of bipolar I disorder, to delay the time to occurrence of mood episodes in the subject treated for acute mood episodes with standard therapy.

In specific embodiments, the oral liquid suspension is administered, such that topiramate is administered in $25\pm5$ mg per mL.

In specific embodiments, the oral liquid suspension is administered, such that topiramate is administered in $25\pm4$ mg per mL.

In specific embodiments, the oral liquid suspension is administered, such that topiramate is administered in $25\pm3$ mg per mL.

In specific embodiments, the oral liquid suspension is administered, such that topiramate is administered in $25\pm2.5$ mg per mL.

In specific embodiments, the oral liquid suspension is administered, such that topiramate is administered in $25\pm1.25$ mg per mL.

In specific embodiments, the oral liquid suspension is administered, such that topiramate is administered in 25 mg per mL.

In specific embodiments, the oral liquid suspension is administered, such that any one of Nos. 1-16

| No. | Volume of oral liquid suspension (mL) | Amount of topiramate (mg) |
|---|---|---|
| 1 | 0.1 | 2.5 ± 0.25 |
| 2 | 0.2 | 5 ± 0.5 |
| 3 | 0.4 | 10 ± 1.0 |
| 4 | 0.5 | 12.5 ± 1.25 |
| 5 | 0.6 | 15 ± 1.5 |
| 6 | 0.8 | 20 ± 2.0 |
| 7 | 1.0 | 25 ± 2.5 |
| 8 | 2.0 | 50 ± 5.0 |
| 9 | 2.5 | 62.5 ± 6.25 |
| 10 | 3.0 | 75 ± 7.5 |
| 11 | 4.0 | 100 ± 10.0 |
| 12 | 5.0 | 125 ± 12.5 |
| 13 | 6.0 | 150 ± 15.0 |
| 14 | 7.0 | 175 ± 17.5 |
| 15 | 8.0 | 200 ± 20.0 |
| 16 | 10.0 | 250 ± 25.0 | is delivered to the subject.

In specific embodiments, the oral liquid suspension is administered, such that any one of Nos. 1-16

| No. | Volume of oral liquid suspension (mL) | Amount of topiramate (mg) |
| --- | --- | --- |
| 1 | 0.1 | 2.5 |
| 2 | 0.2 | 5 |
| 3 | 0.4 | 10 |
| 4 | 0.5 | 12.5 |
| 5 | 0.6 | 15 |
| 6 | 0.8 | 20 |
| 7 | 1.0 | 25 |
| 8 | 2.0 | 50 |
| 9 | 2.5 | 62.5 |
| 10 | 3.0 | 75 |
| 11 | 4.0 | 100 |
| 12 | 5.0 | 125 |
| 13 | 6.0 | 150 |
| 14 | 7.0 | 175 |
| 15 | 8.0 | 200 |
| 16 | 10.0 | 250 | is delivered to the subject.

In specific embodiments, the oral liquid suspension is administered, such that 2.5±0.25 mg topiramate in 0.1 mL of the oral liquid suspension is delivered to the subject.

In specific embodiments, the oral liquid suspension is administered, such that 5.0±0.5 mg topiramate in 0.2 mL of the oral liquid suspension is delivered to the subject.

In specific embodiments, the oral liquid suspension is administered, such that 10±1.0 mg topiramate in 0.4 mL of the oral liquid suspension is delivered to the subject.

In specific embodiments, the oral liquid suspension is administered, such that 12.5±1.25 mg topiramate in 0.5 mL of the oral liquid suspension is delivered to the subject.

In specific embodiments, the oral liquid suspension is administered, such that 15±1.5 mg topiramate in 0.6 mL of the oral liquid suspension is delivered to the subject.

In specific embodiments, the oral liquid suspension is administered, such that 20±2.0 mg topiramate in 0.8 mL of the oral liquid suspension is delivered to the subject.

In specific embodiments, the oral liquid suspension is administered, such that 25±2.5 mg topiramate in 1.0 mL of the oral liquid suspension is delivered to the subject.

In specific embodiments, the oral liquid suspension is administered, such that 50±5.0 mg topiramate in 2.0 mL of the oral liquid suspension is delivered to the subject.

In specific embodiments, the oral liquid suspension is administered, such that 62.5±6.25 mg topiramate in 2.5 mL of the oral liquid suspension is delivered to the subject.

In specific embodiments, the oral liquid suspension is administered, such that 75±7.5 mg topiramate in 3.0 mL of the oral liquid suspension is delivered to the subject.

In specific embodiments, the oral liquid suspension is administered, such that 100±10 mg topiramate in 4.0 mL of the oral liquid suspension is delivered to the subject.

In specific embodiments, the oral liquid suspension is administered, such that 125±12.5 mg topiramate in 5.0 mL of the oral liquid suspension is delivered to the subject.

In specific embodiments, the oral liquid suspension is administered, such that 150±15 mg topiramate in 6.0 mL of the oral liquid suspension is delivered to the subject.

In specific embodiments, the oral liquid suspension is administered, such that 175±17.5 mg topiramate in 7.0 mL of the oral liquid suspension is delivered to the subject.

In specific embodiments, the oral liquid suspension is administered, such that 200±20 mg topiramate in 8.0 mL of the oral liquid suspension is delivered to the subject.

In specific embodiments, the oral liquid suspension is administered, such that 250±25 mg topiramate in 10.0 mL of the oral liquid suspension is delivered to the subject.

In specific embodiments, the oral liquid suspension is administered, such that

2±0.2 mg topiramate in 0.2 mL of the oral liquid suspension, or

5±0.5 mg topiramate in 0.5 mL of the oral liquid suspension, or

25±2.5 mg topiramate in 2.5 mL of the oral liquid suspension, or

100±10.0 mg topiramate in 10 mL of the oral liquid suspension, or

150±15.0 mg topiramate in 15 mL of the oral liquid suspension, or

200±20.0 mg topiramate in 20 mL of the oral liquid suspension is delivered to the subject.

In specific embodiments, the oral liquid suspension is administered, such that 2±0.2 mg topiramate in 0.2 mL of the oral liquid suspension is delivered to the subject.

In specific embodiments, the oral liquid suspension is administered, such that 5±0.5 mg topiramate in 0.5 mL of the oral liquid suspension is delivered to the subject.

In specific embodiments, the oral liquid suspension is administered, such that 25±2.5 mg topiramate in 2.5 mL of the oral liquid suspension is delivered to the subject.

In specific embodiments, the oral liquid suspension is administered, such that 100±10.0 mg topiramate in 10 mL of the oral liquid suspension is delivered to the subject.

In specific embodiments, the oral liquid suspension is administered, such that 150±15.0 mg topiramate in 15 mL of the oral liquid suspension is delivered to the subject.

In specific embodiments, the oral liquid suspension is administered, such that 200±20.0 mg topiramate in 20 mL of the oral liquid suspension is delivered to the subject.

In specific embodiments, the oral liquid suspension is administered, such that upon administration under fasted conditions of a healthy adult subject with epilepsy taking no other medications, the oral liquid suspension exhibits a pharmacokinetic (PK) profile including: AUC, 0-24 (micrograms per hour per ml) of 98-105.

In specific embodiments, the oral liquid suspension is administered, such that upon administration under fasted conditions of a healthy adult subject with epilepsy taking no other medications, the oral liquid suspension exhibits a pharmacokinetic (PK) profile including: $C_{max}$ (micrograms per ml) steady state of 1.5.

In specific embodiments, the oral liquid suspension is administered, such that upon administration under fasted conditions of a healthy adult subject with epilepsy taking no other medications, the oral liquid suspension exhibits a pharmacokinetic (PK) profile including: $T_{max}$(h) of 2-3.

In specific embodiments, the oral liquid suspension is administered, such that upon administration under fasted conditions of a healthy adult subject with epilepsy taking no other medications, the oral liquid suspension exhibits a pharmacokinetic (PK) profile including: $t_{1/2}$(h) of 19-25 (single dose).

In specific embodiments, the oral liquid suspension is administered, such that upon administration under fasted conditions of a healthy adult subject with epilepsy taking no other medications, the oral liquid suspension exhibits a pharmacokinetic (PK) profile including: $t_{1/2}$(h) of 19-25 (multiple dose).

In specific embodiments, the oral liquid suspension is administered, such that upon administration under fasted conditions of a healthy adult subject with epilepsy taking no other medications, the oral liquid suspension exhibits a pharmacokinetic (PK) profile including:

AUC, 0→24 (micrograms per ml) of 98-105;

Cmax (micrograms per ml) steady state of 1.5;
$T_{max}$(h) of 2-3;
$t_{1/2}$(h) of 19-25 (single dose); and
$t_{1/2}$(h) of 19-25 (multiple dose).

In specific embodiments, relative to oral tablets or chewable dispersible tablets containing an equivalent amount of topiramate, administration of the oral liquid suspension results in a lower incidence, severity, and/or duration of adverse reactions including at least one of dizziness, headache, diplopia, ataxia, nausea, blurred vision, somnolence, rhinitis, pharyngitis, rash, vomiting, infection, fever, accidental injury, diarrhea, abdominal pain, tremor, insomnia, somnolence, backpain, fatigue, abdominal pain, and xerostomia.

What is claimed is:

1. An oral liquid suspension comprising:
2,3:4,5-Di-O-isopropylidene-β-D-fructopyranose
  sulfamate (topiramate);
water;
glycerin;
propylene glycol;
polyethylene glycol;
methylparaben;
sodium benzoate;
xanthan gum;
carboxymethyl cellulose;
sodium phosphate; and
microcrystalline cellulose and colloidal silicon dioxide,
  wherein the topiramate is present in 25+/−5 mg/mL.

2. The oral liquid suspension of claim 1, wherein the topiramate present in the oral liquid suspension has the following particle size distribution:
$D_{90}$ of not more than 200 microns,
$D_{50}$ of not more than 100 microns, and
$D_{10}$ of not more than 30 microns.

3. The oral liquid suspension of claim 1, wherein the topiramate present in the oral liquid suspension has the following particle size distribution:
$D_{90}$ of not more than 139 microns,
$D_{50}$ of not more than 64.8 microns, and
$D_{10}$ of not more than 24.65 microns.

4. The oral liquid suspension of claim 1, having a viscosity at 25° C. of 300-400 mPs.

5. The oral liquid suspension of claim 1, having a viscosity at 25° C. of 341.7±10 mPs.

6. The oral liquid suspension of claim 1, having a pH of 7.5-7.9.

7. The oral liquid suspension of claim 1, having a pH of 7.7±0.1.

8. The oral liquid suspension of claim 1, having a specific gravity of not more than 1.1049.

9. The oral liquid suspension of claim 1, having a specific gravity of not more than 1.2.

10. The oral liquid suspension of claim 1, further comprising a flavoring agent.

11. The oral liquid suspension of claim 1, further comprising cherry flavor as a flavoring agent.

12. The oral liquid suspension of claim 1, further comprising a coloring agent.

13. The oral liquid suspension of claim 1, further comprising FD&C red #40 and FD&C yellow #6 as a coloring agent.

14. The oral liquid suspension of claim 1, having a volume of 0.2 mL, 0.5 mL, 2.5 mL, 10 mL, 15 mL, or 20 mL.

15. The oral liquid suspension of claim 1, while packaged in a container, is essentially free from microbial growth for at least 24 months under ambient conditions.

16. The oral liquid suspension of claim 1, while packaged in a container, is essentially free from *Escherichia coli* for at least 24 months under ambient conditions.

17. The oral liquid suspension of claim 1, while packaged in a container, is essentially free from *Burkholderia cepacia* complex for at least 24 months under ambient conditions.

18. The oral liquid suspension of claim 1, which is an immediate release dosage form.

19. The oral liquid suspension of claim 1, which is an immediate release dosage form that exhibits in-vitro dissolution rate more than 88% of drug release within 30 minutes, when said dosage form is placed in a dissolution vessel filled with 900 ml of 0.1N HCL, pH 1.2 maintained at 37±0.5° C. and stirred at a paddle speed of 50 rpm using a USP Type II (paddle) apparatus.

20. The oral liquid suspension of claim 1, further comprising a sweetening agent.

21. The oral liquid suspension of claim 20, wherein the sweetening agent comprises sorbitol, saccharin, sucralose, or any combination thereof.

22. The oral liquid suspension of claim 20, wherein the sweetening agent comprises sorbitol.

23. The oral liquid suspension of claim 20, wherein the sweetening agent comprises saccharin.

24. The oral liquid suspension of claim 20, wherein the sweetening agent comprises sucralose.

25. An oral liquid suspension comprising:
2,3:4,5-Di-O-isopropylidene-β-D-fructopyranose
  sulfamate (topiramate);
water;
glycerin;
propylene glycol;
polyethylene glycol;
methylparaben;
sodium benzoate;
xanthan gum;
carboxymethyl cellulose;
sodium phosphate; and
microcrystalline cellulose and colloidal silicon dioxide,
  wherein the oral liquid suspension has a viscosity at 25°
  C. of 300-400 millipoises.

26. The oral liquid suspension of claim 25, comprising a sweetening agent.

27. The oral liquid suspension of claim 26, comprising sorbitol.

28. The oral liquid suspension of claim 26, comprising saccharin.

29. The oral liquid suspension of claim 26, comprising sucralose.

* * * * *